(12) United States Patent
Araki et al.

(10) Patent No.: US 7,885,826 B2
(45) Date of Patent: Feb. 8, 2011

(54) MEDICAL SERVICE SUPPORT SYSTEM, MEDICAL SERVICE SUPPORT SERVER, AND MEDICAL SERVICE SUPPORT TERMINAL FOR SUPPORTING MEDICAL SERVICE

(75) Inventors: Hiroyuki Araki, Kanagawa (JP);
Shinichi Omori, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/197,507

(22) Filed: Aug. 25, 2008

(65) Prior Publication Data

US 2009/0063195 A1    Mar. 5, 2009

(30) Foreign Application Priority Data

Sep. 5, 2007    (JP)    ............... 2007-230429

(51) Int. Cl.
G06Q 10/00    (2006.01)
G06Q 50/00    (2006.01)
A61B 5/00    (2006.01)
G06F 19/00    (2006.01)

(52) U.S. Cl. ............................................. 705/2; 705/3
(58) Field of Classification Search ............... 705/2, 705/3
See application file for complete search history.

(56) References Cited

U.S. PATENT DOCUMENTS

| | | | | |
|---|---|---|---|---|
| 4,464,172 A | * | 8/1984 | Lichtenstein | ................. 604/65 |
| 4,526,569 A | * | 7/1985 | Bernardi | ................... 604/6.09 |
| 4,670,007 A | * | 6/1987 | Wheeldon et al. | ............. 604/65 |
| 4,718,022 A | * | 1/1988 | Cochran | ................. 210/321.71 |
| 4,785,799 A | * | 11/1988 | Schoon et al. | .............. 604/500 |
| 4,819,653 A | * | 4/1989 | Marks | ......................... 600/486 |
| 4,865,584 A | * | 9/1989 | Epstein et al. | ................. 604/67 |
| 4,898,675 A | * | 2/1990 | Lavender | .................... 210/651 |
| 4,925,444 A | * | 5/1990 | Orkin et al. | ................... 604/80 |
| 4,943,279 A | * | 7/1990 | Samiotes et al. | ............ 604/151 |
| 4,961,428 A | * | 10/1990 | Nikias et al. | ................ 600/512 |

FOREIGN PATENT DOCUMENTS

JP    2002-095641    4/2002

* cited by examiner

*Primary Examiner*—Gerald J. O'Connor
*Assistant Examiner*—Amber Altschul
(74) *Attorney, Agent, or Firm*—Scully, Scott, Murphy & Presser, P.C.

(57) ABSTRACT

In the embodiment of the present invention, when identification information acquired from a drug or instrument to be used on a patient is not included in schedule information stored beforehand, a user is notified to confirm that the identification information is not included in the schedule information. After the notification is provided, in registering the acquired identification information as practice details, the name of a doctor who instructed to use the drug or instrument, which is different from the drug or instrument specified by schedule information, and the reason for the instruction are registered, while associated with the practice details. Accordingly, drugs or instruments necessary for patients can be used in an appropriate manner.

6 Claims, 11 Drawing Sheets

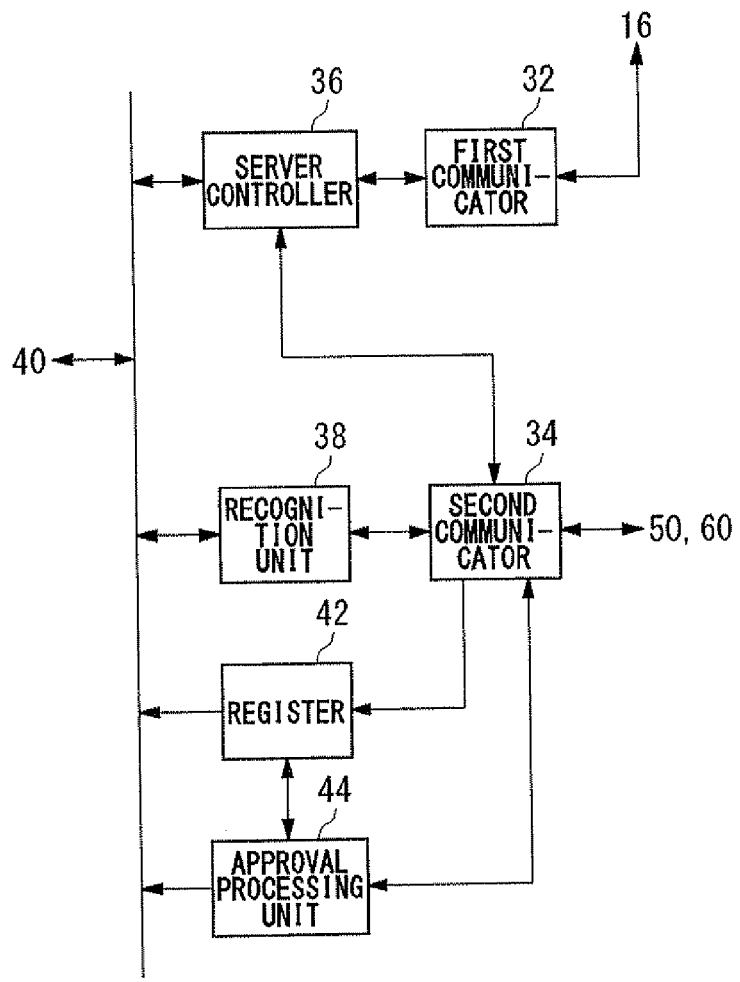

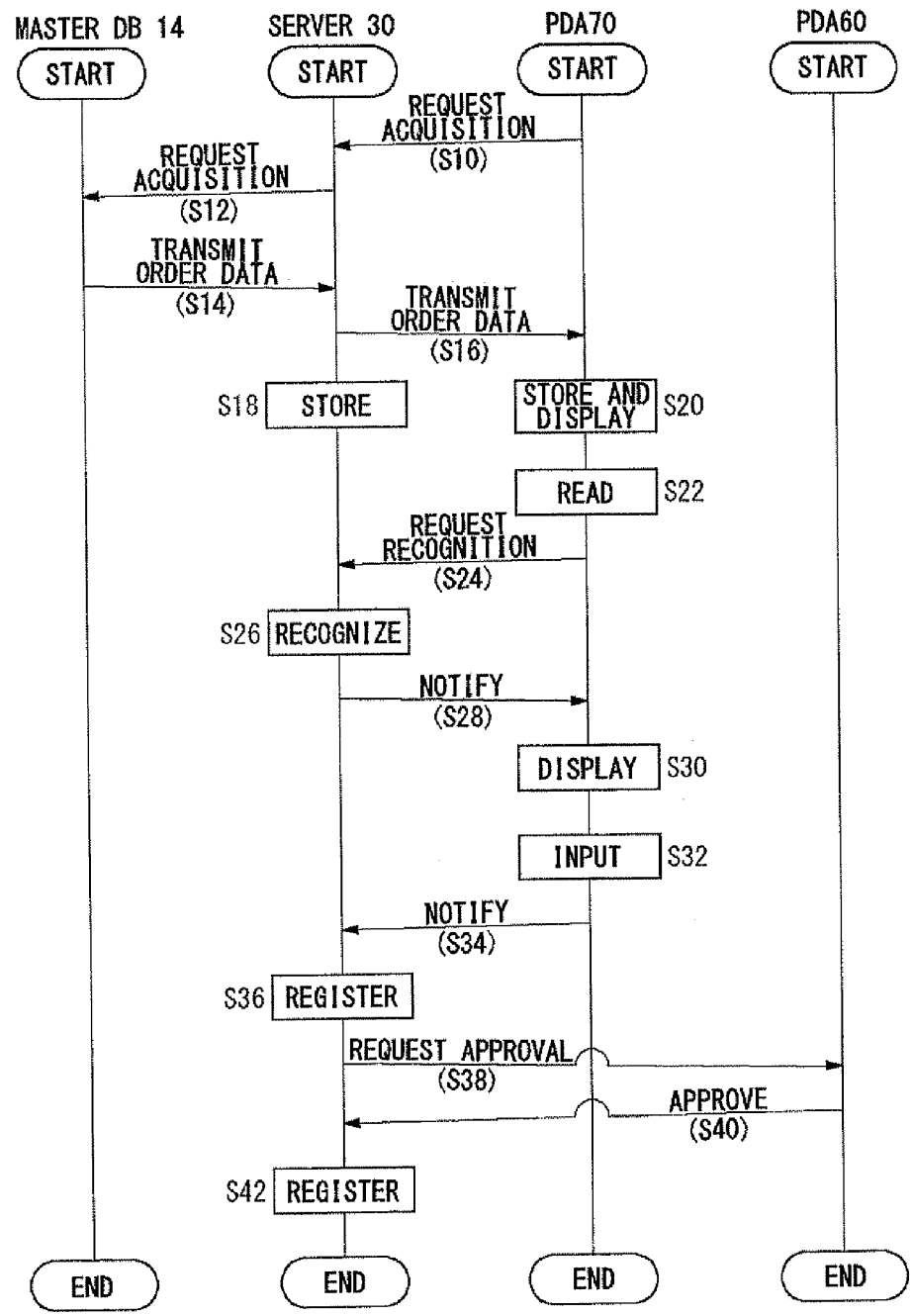

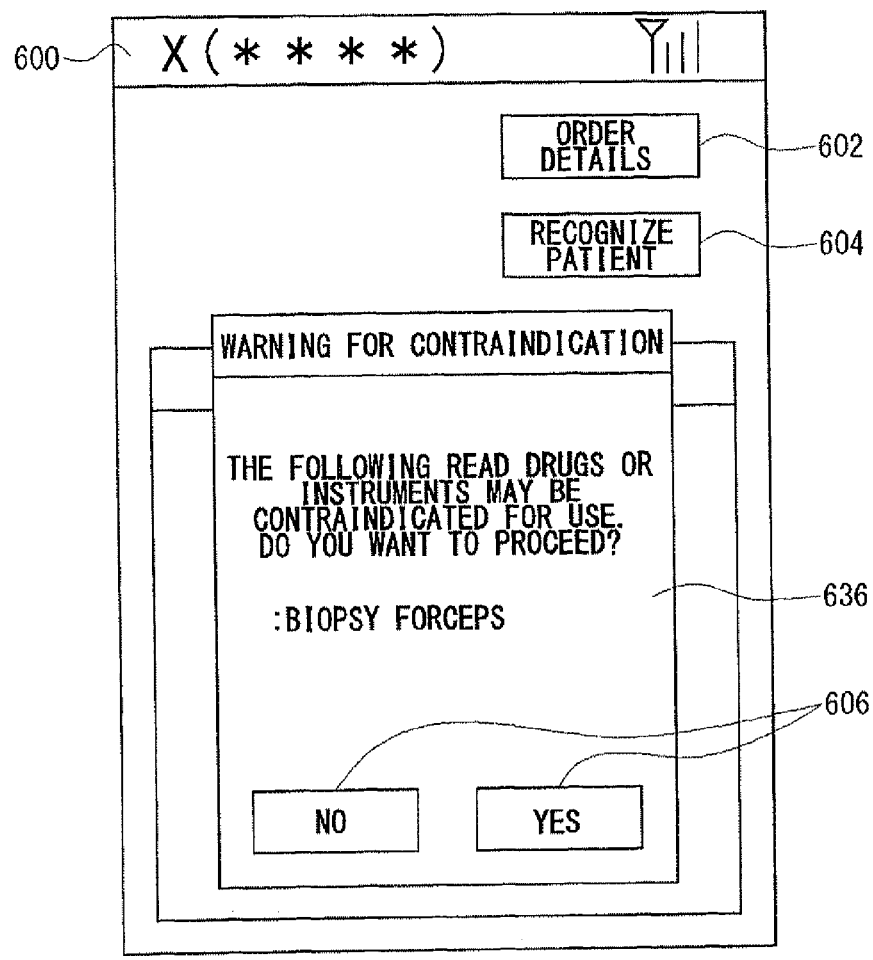

FIG.9

PRACTICE DETAILS INPUT SCREEN [REGISTER] [MODIFY]

PATIENT'S NAME : A ～622

DOCTOR : Y ～624

NURSE : X ～626

PRACTICE DETAILS ～628
　　USE : BIOPSY FORCEPS ～630
　　PRESCRIBING DOCTOR : Y ～632
　　REASON : NOT TAKING ANTICOAGULANT ～634

| 700 | ORDER ID | 2 |
| 702 | PATIENT ID | B01 |
| 704 | SCHEDULE INFORMATION | ADMINISTRATION OF DRUGS |
| 710 | SCHEDULED DRUGS OR THE LIKE | DRUG N |
| 712 | ALTERNATIVE DRUGS OR THE LIKE | DRUG M |

PRACTICE DETAILS INPUT SCREEN [REGISTER] [MODIFY]
— 618  620

PATIENT'S NAME : B —622

DOCTOR : Y —624

NURSE : X —626

PRACTICE DETAILS —628

USE : DRUG M —630

PRESCRIBING DOCTOR : Y —632

REASON : BECAUSE OF Q —634

520

MEDICAL SERVICE SUPPORT SYSTEM, MEDICAL SERVICE SUPPORT SERVER, AND MEDICAL SERVICE SUPPORT TERMINAL FOR SUPPORTING MEDICAL SERVICE

CROSS-REFERENCE TO RELATED APPLICATIONS

This application is based upon and claims the benefit of priority from the prior Japanese Patent Application No. 2007-230429, filed Sep. 5, 2007, the entire contents of which are incorporated herein by reference.

BACKGROUND OF THE INVENTION

1. Field of the Invention

The present invention generally relates to techniques for supporting medical services, and in particular, to medical service support systems, medical service support servers, and medical service support terminals for supporting medical services in hospitals.

2. Description of the Related Art

If it is forbidden to perform a certain medical practice on a patient under specific conditions, nurses or other medical staff should conduct confirmation tasks carefully. However, such confirmation tasks keep nurses more occupied with their tasks. In the related art, there are documents that disclose methods for supporting efficient execution of such confirmation tasks (e.g. see patent document 1). In this method, the details of the medical practice to be performed on a patient and the contraindication information on the medical practices that is not allowed to be performed on the patient are stored in a host computer beforehand. The doctors and nurses input the operation details in terminal devices when they actually perform the medical practices and request recognition from the host computer. When the practice details that are input in the terminal devices fall under the contraindication information, the host computer displays the indication of contraindication on the terminal devices so as to prompt the doctors or the nurses to change the practice details.

[Patent document 1] Japanese patent application: Publication No. 2002-095641

In actual medical practice, drugs or instruments included in pre-registered contraindication information can be used sometimes, depending on a change in the situation, even if the contraindication information indicates a prohibition against using the drugs or instruments. However, it has been difficult to use the drugs and instruments included in the contraindication information in the method mentioned above.

SUMMARY OF THE INVENTION

In this background, a general purpose of the present invention is to provide techniques for supporting medical services in order to use necessary drugs or instruments on patients in an appropriate manner.

According to one embodiment of the present invention, a medical service support system is provided. The medical service support system according to an embodiment of the present invention comprises: a storage operative to store schedule information that specifies a drug or instrument scheduled to be used for a medical practice to be performed on a patient; an acquisition unit operative to acquire identification information from a drug or instrument that will actually be used on the patient, the identification information specifying the drug or instrument to be actually used; a notification unit operative to provide notification in case that the drug or instrument to be actually used that is specified by the identification information acquired by the acquisition unit is not included in the schedule information stored in the storage; and a register operative, when registering as practice details the identification information acquired by the acquisition unit after the notification unit made the notification, to register the name of a doctor who instructed the use of the drug or instrument to be actually used, which is different from the drug or instrument specified by the schedule information, and the reason for the instruction while associating the name and the reason with the practice details.

According to another embodiment of the present invention, a medical service support server is provided. The medical service support server comprises: a storage operative to store schedule information that specifies a drug or instrument scheduled to be used for a medical practice to be performed on a patient; an acquisition unit operative to acquire identification information from a drug or instrument that will actually be used on the patient, the identification information specifying the drug or instrument to be actually used; a determination unit operative to determine whether the drug or instrument to be actually used that is specified by the identification information acquired by the acquisition unit is included in the schedule information stored in the storage; a notification unit operative to provide notification in case the determination unit determines the drug or instrument to be actually used is not included in the schedule information stored in the storage; and a register operative, when registering as practice details the identification information acquired by the acquisition unit after the notification unit makes the notification, to register the name of a doctor who instructed the use of the drug or instrument to be actually used, which is different from the drug or instrument specified by the schedule information, and the reason for the instruction, while associating the name and the reason with the practice details.

According to yet another embodiment of the present invention, a medical service support terminal is provided. The medical service support terminal comprises: a receiving unit operative to receive schedule information from a server, the schedule information specifying a drug or instrument scheduled to be used for a medical practice to be performed on a patient; a storage operative to store the schedule information received by the receiving unit; an acquisition unit operative to acquire identification information from a drug or instrument that will actually be used on the patient, the identification information specifying the drug or instrument to be actually used; a determination unit operative to determine whether the drug or instrument to be actually used that is specified by the identification information acquired by the acquisition unit is included in the schedule information stored in the storage; a notification unit operative to provide notification in case that the determination unit determines the drug or instrument to be actually used is not included in the schedule information stored in the storage; and a register operative, when registering as practice details the identification information acquired by the acquisition unit into the server after the notification unit makes the notification, to register the name of a doctor who instructed the use of the drug or instrument to be actually used, which is different from the drug or instrument specified by the schedule information, and the reason for the instruction, while associating the name and the reason with the practice details.

Optional combinations of the aforementioned constituent elements, or implementations of the invention in the form of methods, apparatuses, systems, recording mediums, and computer programs may also be practiced as additional modes of the present invention. According to the invention, necessary drugs or instruments can be used on patients in an appropriate manner. In addition, the history of the use of the drugs and the instruments on the patients can be correctly recorded.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 2 shows an example of the structure of order data stored in the temporary DB in FIG. 1;

FIG. 3 shows an example of the structure of the server in FIG. 1;

FIG. 5 is a sequence diagram showing an example of operation in the hospital information management system in FIG. 1;

FIG. 6 shows a first example of the order data stored in the temporary DB in FIG. 1;

FIG. 7 shows an example of a first notification screen displayed on the touch-panel display in FIG. 4;

FIG. 9 shows an example of a first confirmation screen displayed on the screen of the PC in FIG. 1;

FIG. 10 shows a second example of the order data stored in a temporary DB in FIG. 1;

FIG. 13 shows an example of a second confirmation screen displayed on the screen of the PC in FIG. 1.

DETAILED DESCRIPTION OF THE INVENTION

Figure 1:
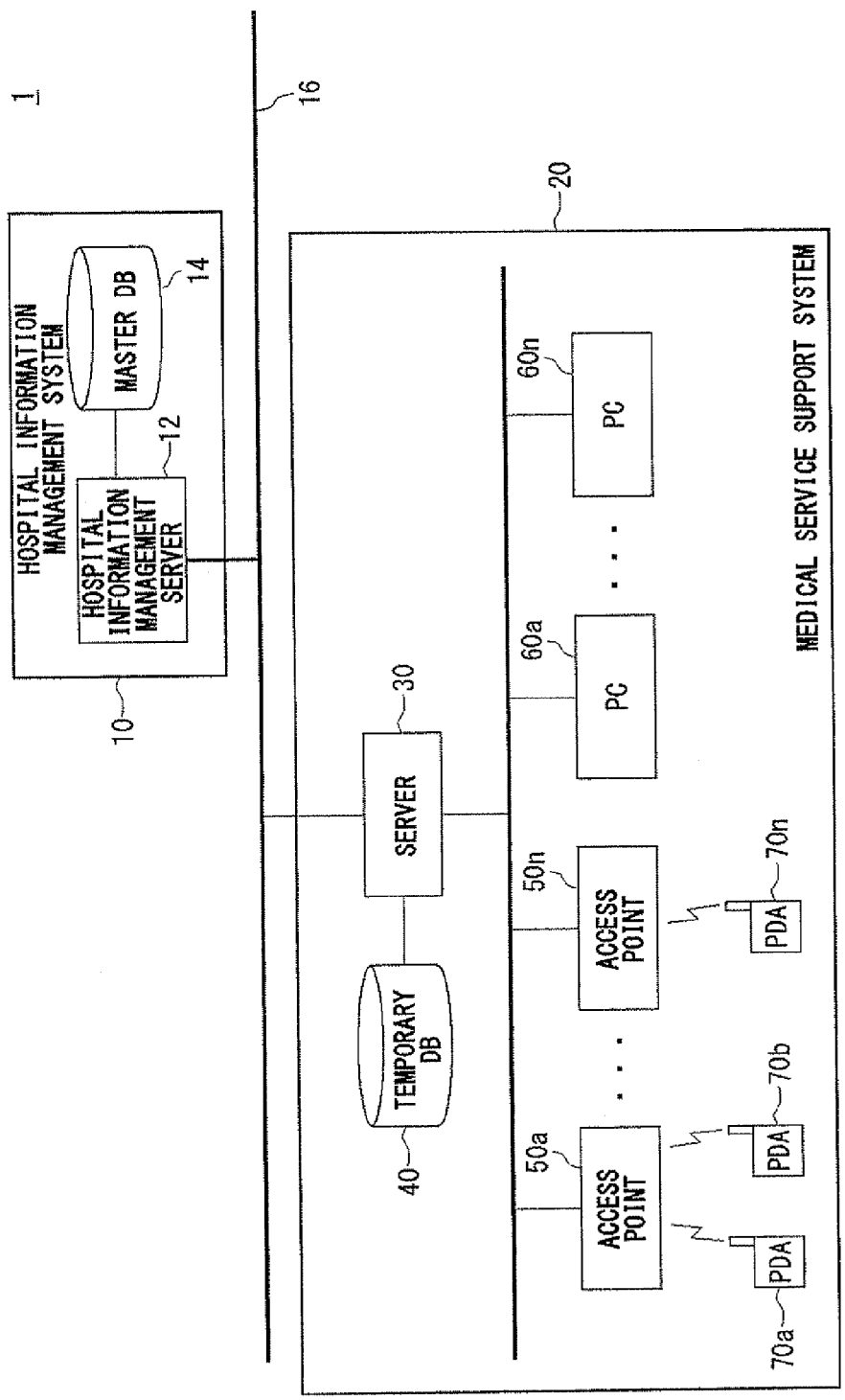
FIG. 1 shows an example of the configuration of a hospital information system, including a medical service support system according to an embodiment of the present invention.

The invention will now be described by reference to the preferred embodiments. This does not intend to limit the scope of the present invention, but to exemplify the invention.

A brief description is now given before focusing on specific features of the present invention. An embodiment of the present invention relates to medical service support systems. The medical service support system is provided with a server and a portable terminal device. With the system, before medical practice is performed on a patient, a nurse or the like performs a recognition process using the portable terminal device in order to recognize a drug or instrument that is to be used in the medical practice. The recognition process is performed by verifying the drug or the like that is to be actually used for the patient against order data stored in the server beforehand and determining whether or not the drug or the like to be used is included in the order data.

The order data is information used for specifying the medical practice to be performed on the patient, and the order data includes schedule information for specifying drugs or instruments that are scheduled to be used on the patient and contraindication information for specifying any drugs and instruments forbidden to be used for the patient. Drugs to be administered, transfusion solutions (e.g., injection solutions and intravenous solutions), and medical instruments, such as biopsy forceps and injection syringes, are hereinafter generically referred to as "drug or the like" in the following for the purpose of explanation.

The order data is created by a doctor before performing a medical practice. However, after the order data is created and by the time the medical practice is performed, the condition of the patient may change and a drug or the like that is not included in the order data may be required to be used on the patient. In most of the cases, such changes are reported to nurses or to other medical staffs orally by the doctor; thus, the nurses have to prepare the drug or the like that is not included in the order data on an ad hoc basis in the place where the medical practices are actually performed (e.g., examination room or operation room). When trying to recognize such drug or the like with the portable terminal device, the recognition fails since the drug or the like are not included in the schedule information stored on the server. Therefore, conventionally, it is required to create another order data concerning the changed medical practice and to perform the recognition process again. Thus, it is difficult to perform the medical practice smoothly.

According to the present invention, even when the medical practice has been changed without prior notice, the drug or the like not included in the order data can be used provided that a certain procedure is executed, for example, if a doctor and a medical staff (e.g., nurse) register, both a reason for using the drug or the like not included in the order data and the name of the doctor who instructed the use of the drug or the like. Therefore, drug or the like to be used on the patients can be appropriately changed without creating order data again, while taking the patients' condition right before the medical practice into considerations.

FIG. 1 shows an example of the configuration of a hospital information system 1 including a medical service support system 20 according to an embodiment of the present invention. The hospital information system 1 is installed in a medical institution such as a hospital and is provided with a hospital information management system 10 serving as a main system and a medical service support system 20 serving as a subsystem. The hospital information management system 10 and the medical service support system 20 are connected so as to communicate with each other via LAN (Local Area Network) 16. The hospital information management system 10 is capable of centrally managing subsystems such as the medical service support system 20 to which the hospital information management system 10 is connected via the LAN 16, in an integrated fashion.

The hospital information management system 10 is provided with a hospital information management server 12 that manages and controls the operation of the subsystems such as the medical service support system 20 and a master database (hereinafter, referred to as "master DB") 14 that records, for example, the data acquired by the subsystems such as the medical service support system 20. In the master DB 14, the authentic order data is recorded, and advanced security measures are taken for preventing the falsification of data from the outside or the like. The hospital information management server 12 accesses the master DB 14 and notifies the medical service support system 20 of the necessary order data in accordance with a request from the medical service support system 20.

The medical service support system 20 includes a server 30, a temporary DB 40, PDA's (Personal Digital Assistants) 70a-70n (hereinafter, generically referred to as "PDA 70"), access points 50a-50n (hereinafter, generically referred to as "access point 50"), and personal computers 60*a*-60*n* (hereinafter, generically referred to as "PC 60") used for inputting and outputting data.

The medical service support system 20 is installed in: a) an outpatient system used for registering data on medical practices such as injections; b) a medical ward system; c) a pharmacy system for dispensing drugs in accordance with the registration of the data on the medical practices; d) a medical profession system for, for example, accounting for the medical practices; e) a nurse system for scheduling and recording medical practices (e.g., coinjections or the like) by the nurse; f) or the like. Specifically, the access point 50 and the PC 60 are provided for the nurse system and the medical ward system with which nurses or other medical staffs perform medical practices. Every nurse and/or other medical staff carries a PDA 70 and inputs and outputs the information on a medical practice or a previous treatment thereof at the site where the medical practice is being performed.

The server 30 controls, for example, the PDA 70 and the PC 60 in the medical service support system 20 and manages necessary data using the temporary DB 40. Also, the server 30 requests order data from the hospital information management system 10 in accordance with a request for acquisition of the order data received from the PDA 70 and then the server 30 acquires the order data stored in the master DB 14. Desired order data is acquired by notifying the hospital information management system 10 of either an identification number attached to the order data to be requested or the identification number of the patient. The server 30 sends the acquired order data to the PDA 70 via the access point 50 and stores the acquired order data in the temporary DB 40.

FIG. 2 shows an example of the structure of order data 200 stored in a temporary DB in FIG. 1. The order data 200 includes an order ID field 700, a patient ID field 702, a schedule information field 704, a condition field 706, and a contraindication information field 708. The ID of the order data is stored in the order ID field 700. The identification information of the patient is stored in the patient ID field 702. The schedule information that specifies a medical practice to be performed on the patient having the patient ID in the patient ID field 702 is stored in the schedule information field 704. Information on the condition of the patient having the patient ID in the patient ID field 702 is stored in the condition field 706. The contraindication information that indicates a drug or the like forbidden to use on the patient having the patient ID in the patient ID field 702 is stored in the contraindication information field 708.

Referring back to FIG. 1, further explanation for each configuration will be given. By storing the order data shown in FIG. 2 into the temporary DR 40 beforehand, the recognition process in response to a request for recognition sent from the PDA 70 can be completed in the server 30 without accessing the hospital information management system 10. Thus, the authorization process can be speeded up. Alternatively, the server 30 may periodically access the master DB 14 of the hospital information management system 10 and may acquire the order data to be stored in the temporary DB 40, independently of the requests for the acquisition of the order data sent from the PDA 70.

The server 30 also performs the recognition process by verifying the identification information of the patient and identification information for specifying the drugs to be actually used that are sent from PDA 70 against the order data stored in the temporary DB 40 in accordance with the request for recognition sent from the PDA 70.

The housing of the PDA 70 has, for example, a size that allows for portability suitable for being carried by a single hand. In addition to the regular PDA features, the PDA 70 has built-in features such as a transmitting and receiving means, including a wireless LAN card that enables the wireless communication with the access point 50 through the wireless LAN, and a reading means for reading identification information. Since the PDA 70 is capable to read identification information, users (e.g., medical staffs including nurses) who carry PDA 70 can accurately and easily read and/or input the identification information of the medical staff, the identification information of a patient on whom the medical practice is performed, or the identification information attached to drug or the like. The users like nurses and medical staffs acquire the order data from the server 30 and instructs the server to perform the recognition process with the read identification information, by manipulating the PDA 70. Further, the PDA 70 has a water-proof structure that is resistant to chemical solutions, and has a structure that is user-friendly for the medical use.

The PC 60 is a stationary terminal, and the medical staff including nurses perform, for example, the input, reference, and confirmation of the data at the location where the PC 60 is placed. A doctor manipulates the PC 60 in order to access the server 30, to extract the cases where drug or the like that are different from the ones indicated by the order data were used, and to display the cases. The doctor performs the approval process in accordance with displayed instruction.

A detailed description is now given. FIG. 3 shows an example of the configuration of the server 30 shown in FIG. 1. The server 30 includes a first communicator 32, a second communicator 34, a server controller 36, a recognition unit 38, a register 42, and an approval processing unit 44.

The server controller 36 controls the first communicator 32 and the second communicator 34. The first communicator 32 performs communication with the hospital information management system 10 via the LAN 16. The second communicator 34 performs communication with the access point 50 or with the PC 60. In the embodiment, the second communicator 34 receives a request for acquisition of order data or a request for recognition of order data sent from the PDA 70 via the access point 50.

Upon receipt of request for the acquisition of the order data, the second communicator 34 forwards the received request for acquisition to the server controller 36. The server controller 36, based on the forwarded acquisition request, makes the first communicator 32 to acquire necessary order data. The first communicator 32 requests the order data from the hospital information management system 10 and acquires the order data, accordingly. After the acquisition of the order data, the server controller 36 stores the acquired order data in the temporary DB 40 and also forwards the order data to the PDA 70 via the second communicator 34.

After the second communicator 34 receives the request for recognition from the PDA 70, the recognition unit 38 accesses the temporary DB 40 and performs the recognition process. The register 42 and the approval processing unit 44 perform the registration process along with the recognition process. More specifically, the recognition process and the registration process are performed as will be described in the following steps.

(1) First, the recognition unit 38 accesses the temporary DB 40 and reads out order data including the identification number of the patient that is included in the request for recognition, accordingly. Next, the recognition unit 38 verifies the identification information of the drug or instrument to be actually used included in the request for recognition against the order data that has been read out. If the drug or the like to be actually used that is specified by the identification information are included in the order data, the recognition unit 38 transmits the information indicating that "the recognition is completed" to the PDA 70 from the second communicator 34.

(2) When the drug or the like to be actually used specified by the identification information are not included in the order data, the recognition unit 38 determines whether the drug or the like to be actually used according to the identification information transmitted from the PDA 70, is included in the contraindication information in the order data. When the drug or the like to be actually used specified by the identification information is included in the contraindication information, the recognition unit 38 allows the second communicator 34 to notify the PDA 70 of the information indicating that "the drug or the like about to be used can possibly be contraindicated". When the drug or the like to be actually used specified by the identification information is not included in the contraindication information, the recognition unit 38 allows the second communicator 34 to transmit signal and notify the PDA 70 of that "the drug or the like about to be used is different from the ones included in the order data". In this case, the second communicator 34 may also signal and notify the PDA 70 of the information indicating that the drug or the like is not contraindicated.

(3) If there is no report from the PDA 70 after a predetermined time period, the recognition unit 38 determines that the use of the drug or the like having supposed to be used actually indicated by the identification information is cancelled, and the recognition process on the drug or the like is completed. On the other hand, if the identification information of the patient, the "name of the doctor who has instructed the use of the drug or the like to be actually used", and the "instruction status" are reported via the second communicator 34, the register 42 stores the reported information in the temporary DB 40 while associating the reported information with the order data of the patient. The instruction status includes the current condition of the patient and the reason for the instruction to use drugs or instruments to be used actually that are not included in the order data.

(4) The approval processing unit 44 executes the approval process by requesting approval from the doctor specified by the "name of the doctor who has instructed the use of the drug or the like". The approval process may include a step where an approval flag is set "ON", the flag being associated with the order data that needs to be approved. After the medical practice is performed, the doctor accesses the server 30 by manipulating the PC 60, extracts, and downloads the order data having the approval flag, which is set "ON". The doctor allows the downloaded order data be displayed, writes a report and approves the order data that needs to be approved. Upon the receipt of the approval from the doctor via the second communicator 34, the register 42 registers the drug or the like and the order data that had been the subject for approval in the temporary DB 40, associating them with information indicating that the approval is completed with success. When approval is not received within a predetermined time period, the approval processing unit 44 may urge the doctor to give approval by emailing from the second communicator 34 to the doctor's email address shown in the "name of the doctor who has instructed the use of the drug or the like".

Figure 4:
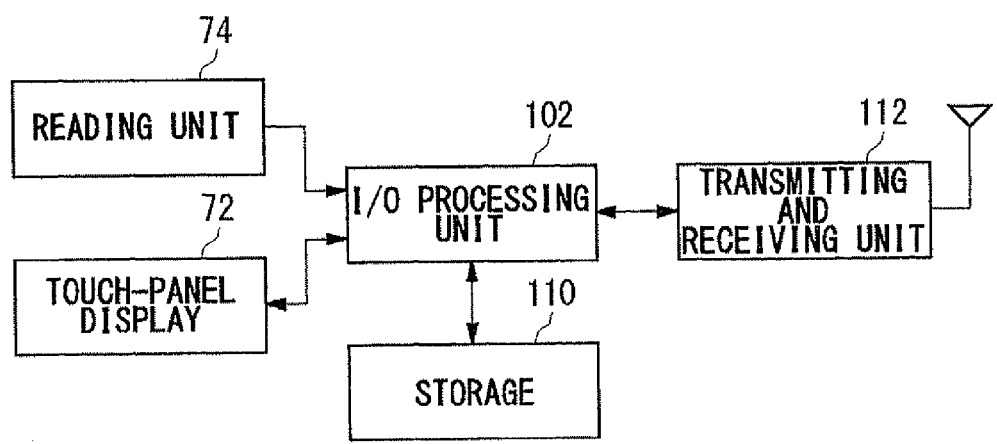
FIG. 4 shows an example of the structure of the PDA in FIG. 1.

FIG. 4 shows a configuration example of the PDA 70 in FIG. 1. The PDA 70 includes a touch-panel display 72, a reading unit 74, an I/O (Input-Output) processing unit 102, a storage 110, and a transmitting and receiving unit 112. The touch-panel display 72 is provided on the surface of the housing of the PDA 70 and is capable of displaying and receiving an input. The reading unit 74 is provided on the upper surface of the housing and includes, for example, an OCR (Optical Character Reader), an optical sensor that reads out identification information using infrared ray or the like, or a detection unit or the like that detects electric waves from a wireless IC tag or the like. The transmitting and receiving unit 112 includes, for example, a wireless card and executes a wireless communication process to and from the access point 50. The PDA 70 is capable of performing (1) a process with respect to order data, and (2) a process with respect to recognition. Configuration of the PDA 70 is described in detail with respect to each function in the following paragraphs.

(1) Process with Respect to Order Data

When there is a request for acquiring the order data input through the touch-panel display 72, the I/O processing unit 102 accepts the request and then requests the order data from the server 30 via the access point 50. When the reading unit 74 completes the process of reading the identification information assigned to the wrist band of the patient, using it as a trigger, the I/O processing unit 102 may request the order data. The order data is received at the transmitting and receiving unit 112. The I/O processing unit 102 stores the acquired order data in the storage 110 and then displays, on the touch-panel display 72, a message indicating that the acquisition of the order is completed.

When there is a request for displaying the acquired order data via the touch-panel display 72, the I/O processing unit 102 accesses the storage 110 and then displays the stored information on the touch-panel display 72.

(2) Process with Respect to Recognition

When the identification information that specifies the drug or the like to be actually used on the patient is acquired via the reading unit 74, the I/O processing unit 102 requests recognition of the drug or the like indicated by the identification information from the server 30. The identification information is included in the request for recognition. As a result of recognition, the transmitting and receiving unit 112 receives one of the signals indicating "recognition is completed", "the drug or the like about to be used can be contraindicated", or "the drug or the like about to be used is not included in the order data". The I/O processing unit 102 displays, on the touch-panel display 72, the message indicated by the received signal.

When the signal indicates "the drug or the like about to be used can be contraindicated" or "the drug or the like about to be used is not included in the order data" as a result of the recognition, the I/O processing unit 102 inquires whether the drug or the like should be used. More specifically, the I/O processing unit 102 displays an inquiry message, for example in case of the contraindication, "The drug or the like about to be used can be contraindicated. Do you proceed to use these drug or the like?" and also displays a "YES" button and "NO" button. Detailed explanation will be given later. Selecting the "YES" button indicates that the user will use the drug or the like that had been subject for recognition and selecting the "NO" button indicates the opposite.

When a user (e.g., a nurse, a medical staff and so on) select the "NO" button by manipulating the touch-panel display 72, the PDA 70 completes the recognition process on the drug or the like and then starts receiving, for example, recognition process on other drug or the like. In contrast, when the "YES" button is selected, the PDA 70 executes the registration process. The I/O processing unit 102 displays on the touch-panel display 72 a message to prompt inputting the "name of the doctor who has instructed the use of the drug or the like" and the "instruction status". More details will follow.

When the "name of the doctor who has instructed the use of the drug or the like" and the "instruction status" are input with respect to the message, the I/O processing unit 102 stores the input "name of the doctor who has instructed the use of the drug or the like" and "instruction status" in the storage 110, associating the "name of the doctor who has instructed the use of the drug or the like" and "instruction status" with the drug or the like specified by the identification information. The I/O processing unit 102 reports the "name of the doctor who has instructed the use of the drug or the like" and the "instruction status" along with the identification information on the drug or the like to be actually used specified by the identification information and completes the registration process.

The above mentioned configurations, from a hardware aspect, can be achieved with an arbitrary computer CPU, memory, and other LSIs, and from a software aspect, the configurations can be achieved with, for example, a program loaded in memory, and a functional block achieved by the solidarity of those components is shown here. Thus, it should be understood by a person skilled in the art that these functional blocks can be realized in a variety of forms by hardware only, software only, or the combination thereof.

Next, the operation of the medical service support system 20 according to the embodiments will be explained as follows. FIG. 5 is a sequence diagram showing an operation example in the hospital information management system 10 in FIG. 1. For the purpose of explanation, the description on processes in the LAN 16 and in the access point 50 is omitted.

A nurse X downloads from the master DB 14 the order data with respect to a patient subject to the medical practice by manipulating the PDA 70. The transmitting and receiving unit 112 of the PDA 70 makes a request to the master DB 14 via the server 30 for acquiring the order data (S10, S12). The master DB 14 transmits the order data to the PDA 70 via the server 30, in response to the request for acquisition of the order data (S14, S16). In addition to forwarding the order data transmitted from the master DB 14 to the PDA 70, the server controller 36 in the server 30 stores the order data in the temporary DB 40 (S18). After downloading the order data, the I/O processing unit 102 in the PDA 70 stores the order data transmitted from the server 30 in the storage 110 and displays the information included in the order data in accordance with the manipulation by the nurse X on the touch-panel display 72 (S20).

The nurse X conducts an interview with a patient A, who is subjected to the medical practice, in order to ask about his or her condition based on the order data displayed on the touch-panel display 72 of the PDA 70. During the interview, the name of the patient A, the health condition such as the body temperature and the blood pressure, physical condition, history of allergies, and the type, amount, and duration of intake of the drugs the patient A currently takes are checked verbally or in writing with the patient A. It is assumed here that a drug or the like, which are identified as contraindicated by the information on contraindication included in the order data, (hereinafter, referred to as "forbidden drug or the like") is found to be able to be used on the patient during the interview with the patient. At this point, the drug or the like once identified as contraindicated but found to be able to be used, is still displayed as the forbidden drug on the touch-panel display 72. However, it is assumed here that the doctor, who receives the result of the interview from the nurse X, determines to use the forbidden drug or the like on the patient and then verbally instructs the nurse X concerning the use of the forbidden drug or the like on the patient.

The nurse X reads, based on the instruction of the doctor, the identification information of the forbidden drug or the like as identification information of the drug or the like to be actually used, by using the reading unit 74 of the PDA 70. The transmitting and receiving unit 112 transmits the identification information that has been read to the server 30 along with the identification information of the patient and requests recognition with respect to the read identification information (S24).

The recognition unit 38 in the server 30 executes the recognition process based on the request for recognition sent from the PDA 70 (S26). In the recognition process, the transmitted identification information and the order data that is registered beforehand are verified against each other. In verification, it is determined whether the drug or the like to be actually used specified by the identification information match the drug or the like included in the order data. When it is determined that there is no match, a determination is made as to whether the drug or the like to be actually used specified by the identification information match the forbidden drug or the like. In this case, it is assumed that the drug or the like to be actually used specified by the identification information transmitted from the PDA 70 is not included in the order data and matches the forbidden drug or the like. Thus, the second communicator 34 determines that the transmitted information does not match the order data and that the drug or the like specified by the transmitted information is considered to be a forbidden drug or the like. The server 30 notifies the PDA 70 of the information indicating that "the drug or the like about to be used can be contraindicated" (S28).

The I/O processing unit 102 in the PDA 70 displays the information received from the server 30 on the touch-panel display 72 (S30). The nurse X inputs, in accordance with the information displayed, the name of the doctor who instructed the use of the drug or the like and the instruction status in which the reason for the instruction is included (S32). After the input, the transmitting and receiving unit 112 notifies the server 30 of the input name of the doctor and the input instruction status (S34). The register 42 in the server 30 registers the name of the doctor and the instruction status, associating the name and the instruction status with the order data (S36).

The approval processing unit 44 in the server 30 executes the approval process with the doctor who instructed the use of the drug or the like (S38). The doctor approves the use of the drug or the like through the PC 60. In case the approval is made by the doctor (S40), the register 42 registers both the drug or the like subject to approval and the order data of the patient in the temporary DB 40, associating the drug or the like and the order data with the information indicating the approval (S42).

A detailed description is now given using a specific example.

The nurse X downloads the order data with respect to a patient for whom he or she is responsible from the master DB 14 by manipulating the PDA 70 (S10-S16). The downloading may be carried out once a day or multiple times a day. After the downloading, the PDA 70 stores the order data transmitted from the server 30 and displays the order data on the screen in accordance with the manipulation by the nurse X (S20). In addition to forwarding the order data acquired from the master DB 14 to the PDA 70, the server 30 stores the order data in the temporary DB 40.

The order data stored in a temporary DS 40 in FIG. 1 is described in detail in the following paragraphs. FIG. 6 shows a first example of first order data 210 stored in a temporary DB 40 in FIG. 1. The number "1" is stored as the order ID in the order ID field 700. The number "A01" is stored as the patient ID of the patient A in the patient ID field 702. The information indicating that an "endoscopy" is scheduled is stored in the schedule information field 704 as schedule information. The information indicating that the patient is "taking anticoagulant" is stored in the condition field 706 as the condition of the patient A. The information indicating that "biopsy forceps" is contraindicated is stored as forbidden drug or the like in the contraindication information field 708.

The nurse X conducts an interview with the patient A, who is subjected to the medical practice, to ask about his or her condition based on the order data displayed on the PDA 70. It is assumed that it has been found as a result of the interview that the patient A has stopped taking anticoagulant for a predetermined period. Accordingly, a biopsy test (hereinafter, abbreviated as "biopsy") can be performed on the patient A.

At this stage, even though a message indicating that a biopsy cannot be performed is displayed on the PDA 70 as part of order data, the doctor Y determines, based on the report from the nurse X, that he/she is going to use biopsy forceps to perform a biopsy.

The nurse X, according to the instruction from the doctor, reads the identification information of the biopsy forceps to be actually used for a biopsy by using the reading unit 74 of the PDA 70 (S22). The PDA 70 transmits the identification information of the biopsy forceps along with the identification information of the patient, and makes a request for recognition with respect to the read identification information to the server 30 (S24).

The server 30 executes the recognition process according to the request for recognition sent from the PDA 70 (S26). Recognition is performed by verifying the identification information of the forceps transmitted from the PDA 70 against the order data that is registered beforehand. In the assumed case, the drug or the like to be used actually specified by the identification information is not included in the order data and matches "biopsy forceps" included in contraindication information. Therefore, the server 30 determines that the transmitted identification information and the order data do not match and that the biopsy forceps are considered to be forbidden instruments. The server 30 notifies the PDA 70 of the information that "the drug or the like (biopsy forceps) about to be used can be contraindicated" (S28).

The PDA 70 displays, for example, as shown in FIG. 7, the information received from the server 30 on the touch-panel display 72 in FIG. 4 (S30). FIG. 7 shows an example of the first notification screen 310 displayed on the touch-panel display 72 in FIG. 4. The first notification screen 310 includes a nurse name field 600, an order detail button 602, a recognize-patient button 604, and a message field 636.

The name of the nurse X and the identification information of the nurse are displayed in the nurse name field 600. The order detail button 602 is a button for displaying the detail of the order data on the screen. The recognize-patient button 604 is a button for starting the process of patient recognition. The process of patient recognition is performed by reading the identification information on a patient's wrist band and comparing the identification information with the patient ID included in the order data. The information transmitted from the server 30 is displayed as an inquiry message in the message field 636. The message field 636 includes selection buttons 606. The selection buttons 606 include a "NO" button and a "YES" button. The nurse responds to the displayed inquiry message by touching either of the buttons.

Figure 8:
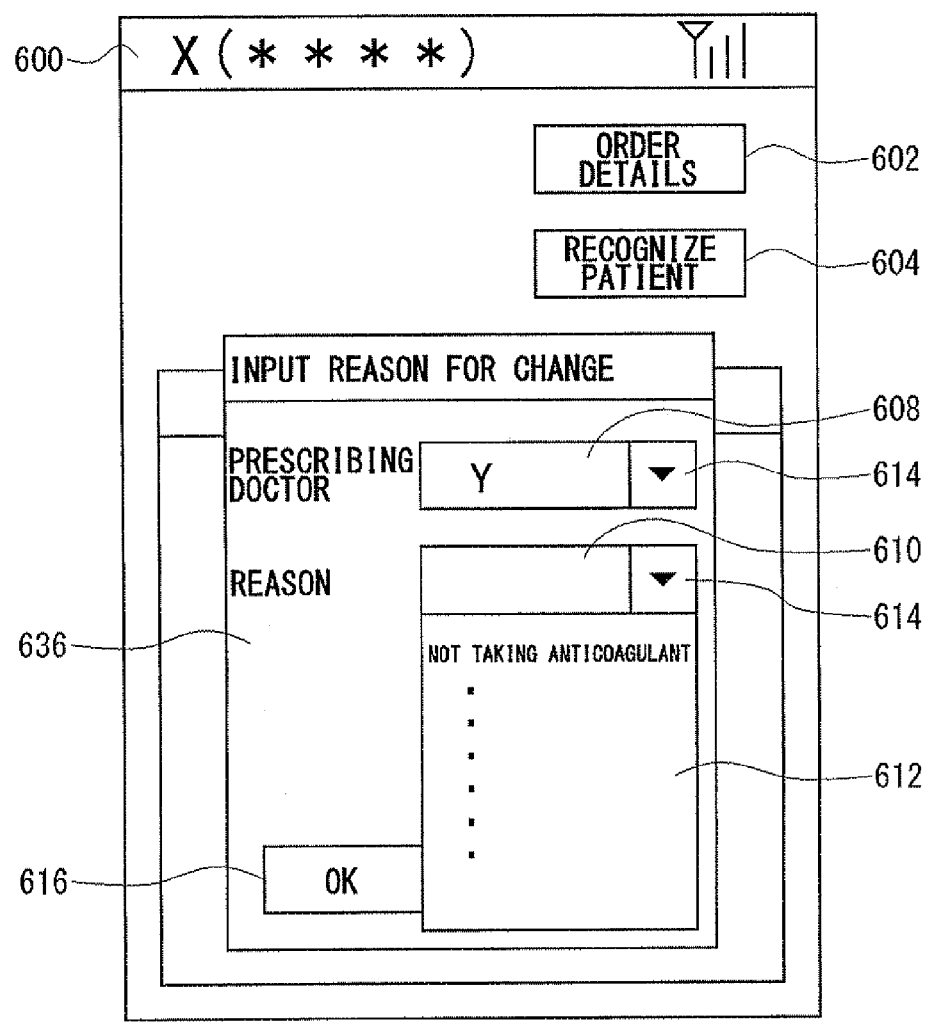
FIG. 8 shows an example of a first input screen displayed on the touch-panel display in FIG. 4.

When the nurse X touches the "YES" button of the selection buttons 606, an input screen shown in FIG. 8 is displayed on the touch-panel display 72 in FIG. 4. FIG. 8 shows an example of the first input screen 410 displayed on the touch-panel display 72 in FIG. 4. The first input screen 410 includes the nurse name field 600, the order detail button 602, the recognize-patient button 604, and the message field 636. The message field 636 includes a prescribing doctor field 608, a reason field 610, a reason list field 612, a list display button 614, and an OK button 616.

In the first input screen 410, the nurse X first selects the name of the doctor Y who instructed the use of the forbidden drug or the like and then inputs the name of the doctor Y in the prescribing doctor field 608. The nurse X displays the list of reasons in the reason list field 612 by touching the list display button 614 in the reason field 610. The nurse X selects a reason "Not taking anticoagulant" in the reason list field 612 as a reason for the instruction. The input process is completed by touching the OK-button 616, accordingly. After the inputting, the PDA 70 notifies the server 30 of the input name of the doctor Y and the instruction status, which includes the reason for the instruction (S34). The server 30 registers the notified name of the doctor Y and the instruction status, while associating the name and the instruction status with the order data (S36).

The server 30 executes the approval process with respect to the doctor Y who instructed the use of the drug or the like (S38). The doctor Y manipulates the PC 60 to access the server 30, in order to extract the order data that requires approval, and to display such information as in FIG. 9 on the screen. FIG. 9 shows an example of the first confirmation screen 510 displayed on the screen of the PC 60 in FIG. 1.

The first confirmation screen 510 includes a register button 618, a modify button 620, a patient name field 622, a doctor name field 624, a nurse field 626, and a practice detail field 628. The register button 618 is a button which can be selected by a pointer manipulated by a doctor, for example, a mouse or the like. The doctor selects the register button 618 when approving the information displayed on the first confirmation screen 510. The modify button 620 is a button to be selected when the displayed contents need to be corrected.

The name "A" of the patient A is displayed in the patient name field 622. The name "Y" of the doctor in charge of the patient A is displayed in the doctor name field 624. The name "X" of the nurse in charge of the patient A is displayed in the nurse name field 626. The practice detail field 628 includes a drug or the like field 630, the prescribing doctor's name field 632, and the reason for the instruction field 634. The drug or the like field 630 is a field where the names of the to-be-used drug or the like are displayed, and the name "biopsy forceps" is displayed in this example. The name "Y" of the doctor who has instructed the use of the drug or the like in the drug or the like field 630 is displayed in the prescribing doctor's name field 632. The reason for using of the drug or the like in the drug or the like field 630, "Not taking anticoagulant", is displayed in the reason for the instruction field 634.

When the doctor Y approves the practice details displayed on the first confirmation screen 510 by pointing the register button 618 (S40), the server 30 registers the biopsy forceps subject to approval and the order data of the patient A in the temporary DB 40, associating the biopsy forceps and the order data with the information indicating approval of the practice details (S42). Although not shown in the figure, when the order data requiring approval is extracted in S38, the first confirmation screen 510 in FIG. 9 may be displayed after displaying a warning that indicates the presence of order data that need to be approved. When displaying the order data obtained from the server 30 in a list, the order data that requires approval may be displayed in display formats that are different from the regular display format of the order data, for example, using indicators such as marks, icons, or the likes.

Owing to the features as described above, the PDA 70 can be used efficiently in the hospital information system 1 in the embodiment. As a result, the status of the medical practice can be recorded and referred to in real time. The nurse who carries the PDA 70 can confirm, during medical practice, the details of task scheduling for the medical practice using the PDA 70. Since the scheduled medical practice can be performed after checking the details of the task scheduling, the medical practice can be performed smoothly. Even when the practice details of the medical practice need to be changed in accordance with a change in the patient's condition, by registering the name of the doctor and the reason for the change, the practice details can be changed in an appropriate manner.

An exemplary variation of the present invention is now shown in the following. First, the outline of the exemplary variation is described in detail. The same numerals represent the same or corresponding elements previously stated in the embodiments, and the description thereof is simplified. The exemplary variation relates to the medical service support system and has a configuration similar to the one in FIG. 1, as in the case of the previously stated embodiment.

The difference from the previously stated embodiment is that the master DB 14 stores substitute information for every drug and instrument in addition to the order data. The substitute information is the information indicating the corresponding relation between one drug or instrument and an alternative drug or instrument that can be used in place of the first drug or instrument. Since substitute information for every drug and instrument is stored, the data size of the substitute information that is registered in the master DB 14 is large.

Thus, the server 30 downloads only the necessary substitute information from the master DB 14 to the temporary DB 40. For example, when the order data is requested from the PDA 70, the order data requested and the substitute information for drugs and instruments included in the order data may be downloaded and stored in the temporary DB 40.

The operation of the medical service support system 20 according to the exemplary variation is described in detail in accordance with each process in the sequence diagram in FIG. 5 previously stated, using a specific example in the following paragraphs.

First, the nurse X accesses the server and then downloads the order data with respect to a patient for whom he or she is responsible by manipulating the PDA 70 (S10-S16). The nurse X also displays the downloaded order data on the PDA 70 screen (S20). The server obtains, along with the order data, the substitute information related to the order data, associates the order data and the substitute information, and stores the resulting information in the temporary DB 40 (S18).

An example of the order data or the like stored in a temporary DB 40 is shown in FIG. 10. FIG. 10 shows a second example of second order data 220 stored in a temporary DB 40 in FIG. 1. The second example of the order data or the like includes the order ID field 700, the patient ID field 702, the schedule information field 704, a scheduled drug or the like field 710, and an alternative drug or the like field 712. The number "2" is stored in the order ID field 700 as the identification information of the order data. The number "B01" is stored as the identification information of the patient B in the patient ID field 702. The information indicating "administration of drugs" is stored as schedule information in the schedule information field 704. The name of a drug "drug N" is stored as a scheduled drug in the scheduled drug or the like field 710. The name of a drug "drug M" is stored as an alternative drug in the alternative drug or the like field 712.

The nurse X conducts an interview with the patient B who will be subjected to the medical practice in order to check his or her condition. It is assumed here that the patient B, as a result of the interview, is found to have a previous illness Q. It is also assumed that, while the drug N cannot be administered to the patient having the previous illness Q, the drug M can be administered to the same patient. Thus, the drug N cannot be administered to the patient B in this case. The nurse X seeks for the doctor Y's instructions, and the doctor Y makes a determination to use the drug M instead of the drug N in this situation.

The nurse X, according to the instruction from the doctor, reads the identification information of the drug M by using the reading unit 74 of the PDA 70 (S22). The PDA 70 transmits the identification information of the drug M, along with the identification information of the patient, and performs a request for recognition with respect to the read identification information of the drug M to the server 30 (S24).

The server 30 executes the recognition process based on the request for recognition sent from the PDA 70 (S26). In the recognition process, the transmitted identification information of the drug or instrument to be actually used and the order data that is registered beforehand are verified against one other. In the verification process, the determination is made as to whether the drug or the like to be actually used specified by the identification information match the drug or the like included in the order data. When it is determined that there is no match, a determination is made as to whether the drug or the like to be actually used specified by the identification information match the drug or the like specified by the substitute information.

In this example, the identification information of the drug M transmitted from the PDA 70 does not match that of the drug N included in the order data but does match that of the drug M included in the substitute information. Therefore, the server 30 makes the determination that the transmitted identification information of the drugs or instrument to be actually used and the order data do not match each other and that the drug M is an alternative drug to the drug N, and notifies the PDA 70 of that, accordingly (S28).

Figure 11:
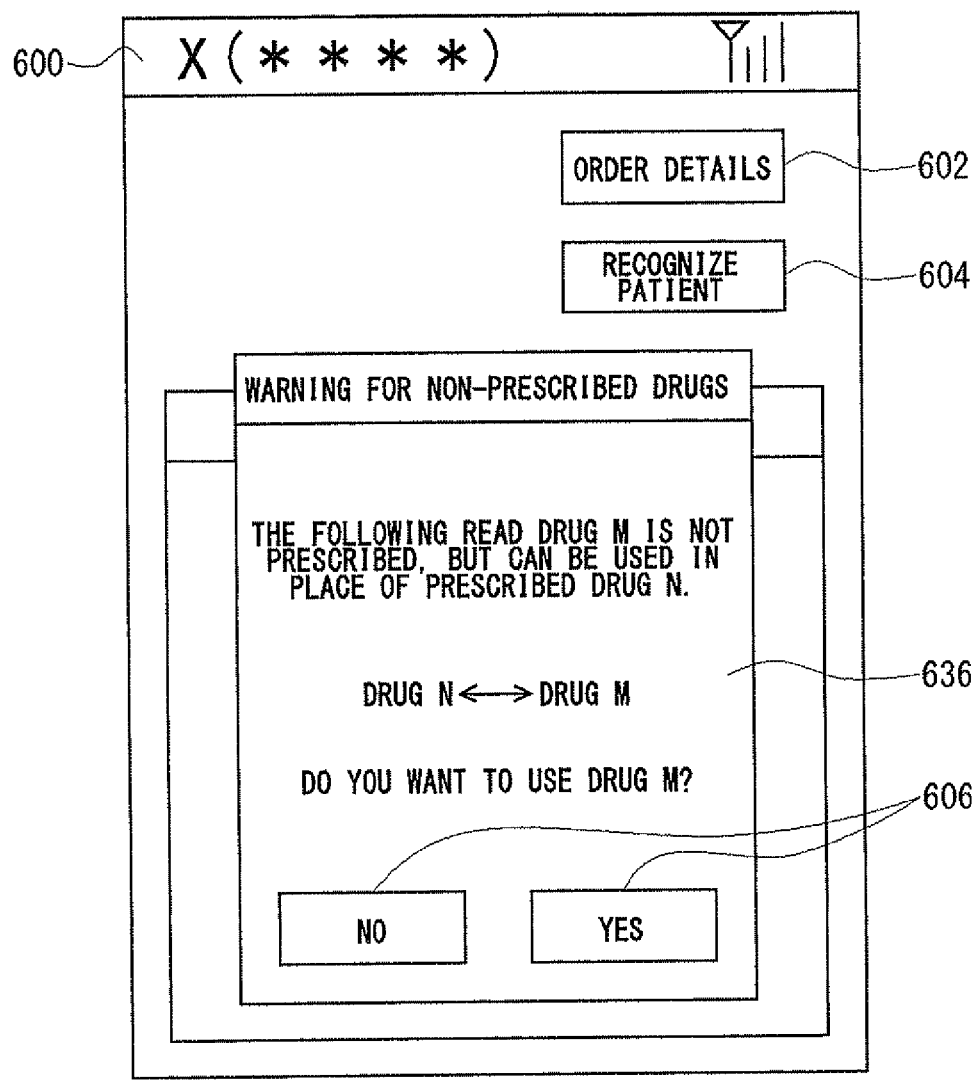
FIG. 11 shows an example of a second notification screen displayed on the touch-panel display in FIG. 4.

The PDA 70 displays the information received from the server 30, in accordance with the notification, on the touch-panel display 72 in FIG. 4 as shown in FIG. 11 (S30). FIG. 11 shows an example of the second notification screen 320 displayed on the touch-panel display 72. The second notification screen 320 is same as the first notification screen 310 shown in FIG. 7 except for the message displayed in the message field 636. The information of which the PDA 70 is notified from the server 30 is displayed in the message field 636 as shown in the figure.

Figure 12:
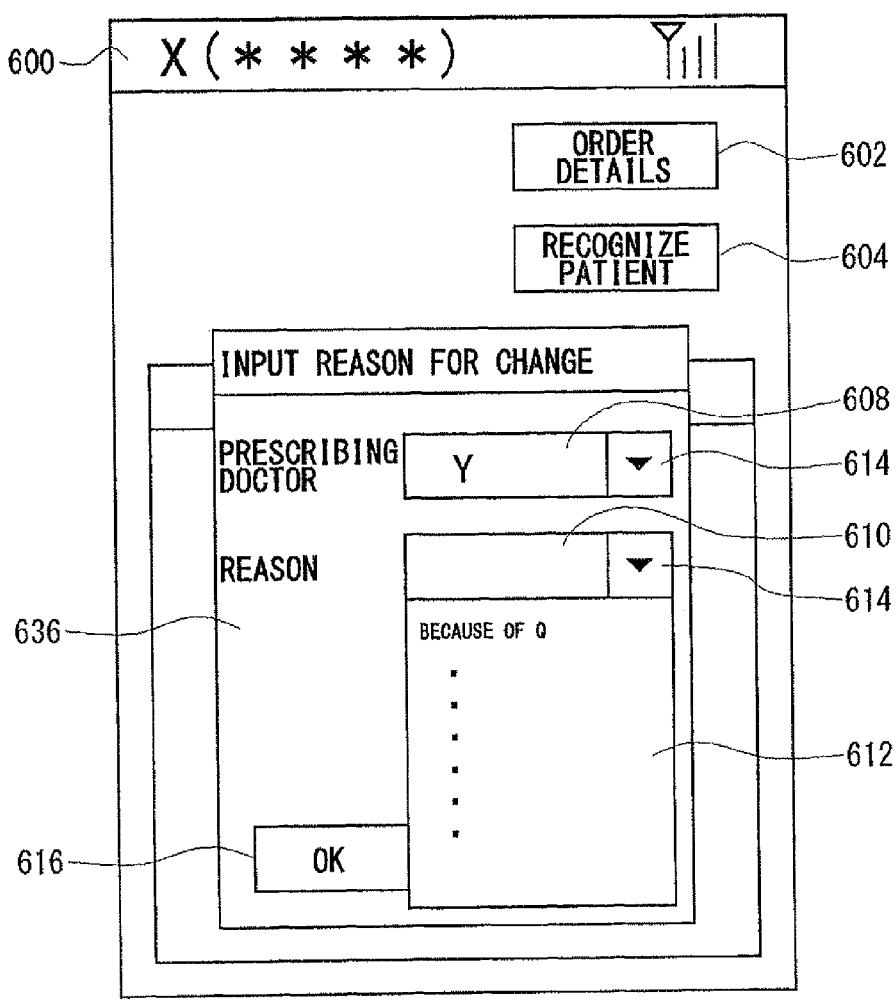
FIG. 12 shows an example of a second input screen displayed on the touch-panel display in FIG. 4.

When the nurse X touches the "YES" button of the selection button 606, an input screen shown in the screen in FIG. 12 is displayed on the touch-panel display 72 in FIG. 4 (S30). FIG. 12 shows an example of the second input screen 420 displayed on the touch-panel display 72. The second input screen 420 is same as the first input screen 410 shown in FIG. 8 except the reason list displayed in the reason list field 612.

The nurse X then inputs the name of the doctor Y who instructed the use of the drug M and the reason for the instruction, "due to Q", by selecting an appropriate one from the reason list (S32). After the input, the PDA 70 notifies the server 30 of the input name of the doctor Y and the instruction status, which includes the reason for the instruction (S34). The server 30 registers the notified name of the doctor Y and the instruction status, associating the name and the instruction status with the order data (S36).

The server 30 executes the approval process with respect to the doctor Y who instructed the use of the drug or the like (S38). The doctor Y manipulates the PC 60 so as to display the information that requires approval as shown in FIG. 13. FIG. 13 shows an example of the second confirmation screen 520 displayed on the screen of the PC 60 in FIG. 1. The second confirmation screen 520 is same as the first confirmation screen 510 shown in FIG. 9 except for the information displayed in the patient name field 622, the drug or the like field 630, the prescribing doctor's name field 632, and the reason for the instruction field 634, the explanation on the second confirmation screen 520 is omitted. The name of the patient B is displayed in the patient name field 622, and the details input in the input screen in FIG. 12 are displayed in the drug or the like field 630 and the prescribing doctor's name field 632. When the doctor Y approves the practice details displayed on the second confirmation screen 520 by indicating or pressing the register button 618 (S40), the server 30 registers the drug M subject to approval and the order data of the patient B in the temporary DB 40, associating the drug M and the order data with the information indicating the approval (S42).

When the identification information of a drug L, which is different from both the drug N and the drug M, is read by the PDA 70 in step S22 stated previously, it is determined, at the recognition step of the server 30 (S26), that the drug L is not included in either the order data nor the recognized alternative drugs. In this case, in step S30, the PDA 70 displays the screen shown in FIG. 14, on the touch-panel display 72 in FIG. 4 (S30), and the recognition process of the drug L is forcibly terminated.

Figure 14:
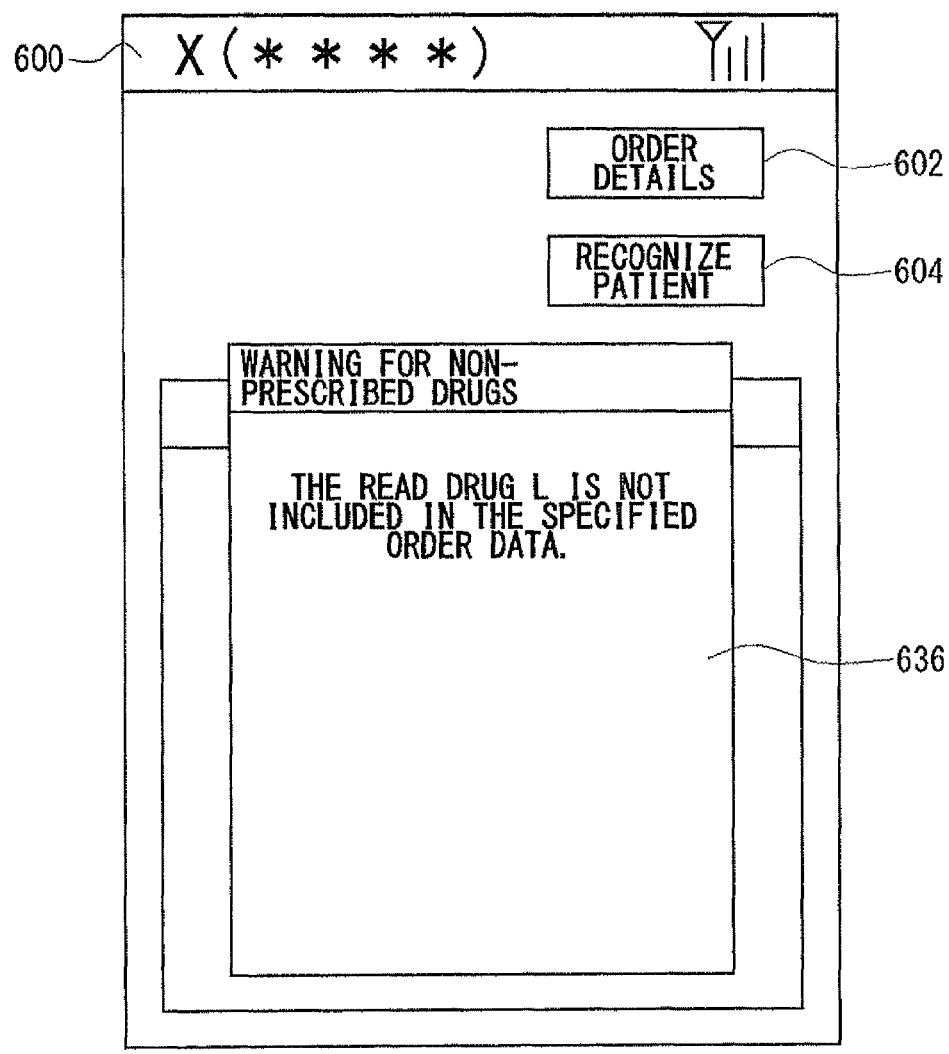
FIG. 14 shows an example of a third notification screen displayed on the touch-panel display in FIG. 4.

FIG. 14 shows an example of a third notification screen 330 displayed on the touch-panel display 72 in FIG. 4. The third notification screen 330, which is different from the second notification screen 320 shown in FIG. 11, does not display the selection button 606. This is because that the drug L cannot be used in place of the drug N and also for the purpose of not displaying the input screen for inputting the name of the doctor and the instruction status.

Because of having the features stated above, the recognition process can be completed promptly even when the alternatives are used for the drug and the like included in the order data registered beforehand. When the identification information of the drug or the like that cannot be used as alternatives is read, a nurse cannot perform a registration process, and the recognition of the drug or the like does not succeed. Thus, a misuse of the drugs can be prevented.

Described above is an explanation based on the preferred embodiments of the present invention. These embodiments are intended to be illustrative only and it will be obvious to those skilled in the art that various modifications to constituting elements and processes could be developed and that such modifications are also within the scope of the present invention.

In the embodiments, the case in which the recognition process is performed in the server 30 is explained; however, the recognition process can also be performed in other element than in the server 30, for example, in the PDA 70. In this case, the PDA 70 has to obtain the order data beforehand, including information on forbidden drugs and the substitute information, from the server 30. With this, there is no time lag for the inquiry; thus, the recognition process can be promptly performed.

What is claimed is:

1. A medical service support system comprising:
a database operatively connected to a computer to store information of a drug or instrument scheduled to be used for a medical practice to be performed on a patient;
an acquisition unit operatively connected to a computer to read identification information attached to a drug or instrument that will actually be used on the patient and operative to acquire the identification information which specifies the drug or instrument to be actually used;
a determination unit operatively connected to a computer to determine whether the drug or instrument to be actually used that is specified by the identification information acquired by the acquisition unit matches the drug or instrument scheduled to be used for the medical practice stored in the database;
a notification unit operatively connected to a computer to provide notification in case that the drug or instrument to be actually used is determined by the determination unit not to match with the drug or instrument scheduled to be used for the medical practice not included in the schedule information stored in the database; and
a register operatively connected to a computer, when registering as practice details the identification information acquired by the acquisition unit after the notification unit made the notification, to register the name of a doctor who instructed the use of the drug or instrument to be actually used, which is different from the drug or instrument scheduled to be used for the medical practice, and the reason for the instruction while
associating the name and the reason with the practice details.

2. The medical service support system according to claim 1, further comprising:
an approval reception unit operatively connected to a computer, after the register makes the registration, to receive approval from a doctor who instructed the use of the drug or instrument to be actually used, which is different from the drug or instrument scheduled to be used for the medical practice, wherein
the register, in case the approval reception unit receives the approval, registers information indicating that the approval has been received, associating the information and the practice details with each other.

3. The medical service support system according to claim 1, wherein
the database further stores substitute information that associates a drug or instrument and at least one alternative drug or instrument that can be used in place of the drug or instrument with each other,
the determination unit, in case of having determined that the drug or instrument to be actually used does not match the drug or instrument scheduled to be used for the medical practice stored in the database, further determines whether the drug or instrument to be actually used is included in the alternative drugs or instruments that can be used in place of the drug or instrument scheduled to be used for the medical practice, and
the register, if the determination unit determines that the drug or instrument to be actually used is included in the alternative drugs or instruments, registers the name of a doctor who instructed the use of the drug or instrument to be actually used and the reason for the instruction.

4. The medical service support system according to claim 1, wherein
the database stores condition information specifying patient's condition and contraindication information specifying a drug or instrument forbidden to use for the patient's condition, associating the condition information and the contraindication information with each other,
the determination unit, when having determined that the drug or instrument to be actually used that is specified by the identification information acquired by the acquisition unit does not match the drug or instrument scheduled to be used for the medical practice stored in the database, further determines whether the drug or instrument to be actually used is included in the forbidden drugs or instruments specified by the contraindication information associated with the condition information of the patient on whom the medical practice is to be performed, and the register, in case that the determination unit determines that the drug or instrument to be actually used is included in the forbidden drugs or instruments, registers the name of the doctor who instructed the use of the drug or instrument to be actually used and the reason for the instruction.

5. A medical service support server, comprising:

a database operatively connected to a computer to store information of a drug or instrument scheduled to be used for a medical practice to be performed on a patient;

an acquisition unit operatively connected to a computer to read identification information attached to a drug or instrument that will actually be used on the patient and operative to acquire the identification information which specifies the drug or instrument to be actually used;

a determination unit operatively connected to a computer to determine whether the drug or instrument to be actually used that is specified by the identification information acquired by the acquisition unit matches the drug or instrument scheduled to be used for the medical practice stored in the database;

a notification unit operatively connected to a computer to provide notification in case the determination unit determines the drug or instrument to be actually used does not match the drug or instrument scheduled to be used for the medical practice stored in the database; and a register operatively connected to a computer, when registering as practice details the identification information acquired by the acquisition unit after the notification unit makes the notification, to register the name of a doctor who instructed the use of the drug or instrument to be actually used, which is different from the drug or instrument scheduled to be used for the medical practice, and the reason for the instruction, while associating the name and the reason with the practice details.

6. A medical service support terminal, comprising:

a receiving unit operatively connected to a computer to receive information of a drug or instrument scheduled to be used for the medical practice to be performed on a patient from a server;

a database operatively connected to a computer to store the information of a drug or instrument scheduled to be used for the medical practice received by the receiving unit;

an acquisition unit operatively connected to a computer to read identification information attached to a drug or instrument that will actually be used on the patient and operative to acquire the identification information which specifies the drug or instrument to be actually used;

a determination unit operatively connected to a computer to determine whether the drug or instrument to be actually used that is specified by the identification information acquired by the acquisition unit matches the drug or instrument scheduled to be used for the medical practice stored in the database;

a notification unit operatively connected to a computer to provide notification in case that the determination unit determines the drug or instrument to be actually used does not match the drug or instrument scheduled to be used for the medical practice stored in the database; and a register operatively connected to a computer, when registering as practice details the identification information acquired by the acquisition unit into the server after the notification unit makes the notification, to register the name of a doctor who instructed the use of the drug or instrument to be actually used, which is different from the drug or instrument scheduled to be used for the medical practice, and the reason for the instruction, while associating the name and the reason with the practice details.

* * * * *